US005728531A

United States Patent [19]

Yamada et al.

[11] Patent Number: 5,728,531
[45] Date of Patent: Mar. 17, 1998

[54] METHOD OF DETECTING NUCLEIC ACID

[75] Inventors: Yukio Yamada, Tsushima; Osamu Asami, Konan; Hiroko Uchiyama, Nagoya; Hidehiko Sugiyama, Aichi-gun; Satoshi Fujita, Nisshin; Takekazu Yamamoto, Tokyo; Naoto Kagiyama, Sapporo; Masayoshi Momiyama, Sapporo; Yasumitsu Kondoh, Sapporo, all of Japan

[73] Assignees: Kabushiki Kaisha Toyota Chuo Kenkyusho, Aichi; Aisin Seiki Kabushiki Kaisha, Kariya, both of Japan

[21] Appl. No.: 624,116

[22] Filed: Mar. 29, 1996

[51] Int. Cl.$^6$ .............................. C12Q 1/68; C12N 15/00; C07H 21/04
[52] U.S. Cl. ........................... 435/6; 935/77; 935/78; 536/243; 435/65
[58] Field of Search ................ 435/6, 65; 536/24.3, 536/23.1

[56] References Cited

U.S. PATENT DOCUMENTS 5,354,657  10/1994  Holtke et al. .

FOREIGN PATENT DOCUMENTS

| 0 133 671 | 3/1985 | European Pat. Off. . |
| 0 324 468 | 7/1989 | European Pat. Off. . |
| 61-115094 | 6/1986 | Japan . |
| 1-215300 | 8/1989 | Japan . |
| 7-184696 | 7/1995 | Japan . |
| 08089296 | 4/1996 | Japan . |
| WO 85/05685 | 12/1985 | WIPO . |
| WO 93/16096 | 8/1993 | WIPO . |

OTHER PUBLICATIONS

Matthews et al., Analytical Biochemistry 169: 1–25 (1988).
FEBS Lett., vol. 202, No. 1, pp. 27–31, 1986, J. Eberle, et al., "Monoclonal Antibodies Against $GA_{13}$–Imide Recognize the Endogenous Plant Growth Regulator, $GA_4$, and Related Gibberellins".
Plant Cell Physiology, vol. 32, No. 4, pp. 505–510, 1991, Masatoshi Nakajima, et al., "Preparation and Validation of an Antisueum Specific for Non–Derivatized Gibberellins".

Primary Examiner—Stephanie W. Zitomer
Assistant Examiner—Ethan Whisenant
Attorney, Agent, or Firm—Oblon, Spivak, McClelland, Maier & Neustadt, P.C.

[57] ABSTRACT

A method of detecting nucleic acid utilizes hybridization between the nucleic acid to be detected which is present on an immobilizing support and a DNA probe which is complementary to at least a portion of the desired nucleotide sequence of the nucleic acid. The present DNA probe includes a hapten attached via a linker which a hapten is gibberellin or a gibberellin derivative. After hybridization by reaction between the nucleic acid to be detected and the DNA probe, the unreacted DNA probe is removed, and then labelled anti-hapten antibody is allowed to bind with the DNA probe of the hybrid and the labelling is used to detect the nucleic acid.

Accordingly, stable detecting sensitivity may be achieved regardless of the label mixing ratio or labelling ratio, and thus regardless of the nucleotide sequence composition of the nucleic acid being tested.

20 Claims, 2 Drawing Sheets

METHOD OF DETECTING NUCLEIC ACID

BACKGROUND OF THE INVENTION

1. Field of the Invention

The present invention relates to a method of detecting nucleic acid, in order to detect whether or not a nucleotide sequence of interest is present in a nucleic acid.

2. Description of the Related Art

Conventional methods for detecting nucleic acid detect specific nucleotide sequences by reacting a specific nucleotide sequence of interest in a DNA sample immobilized on a membrane or other immobilizing support with a DNA probe which binds therewith in a complementary manner, after first attaching a radioisotope, fluorescent dye or other labelling substance thereto, and then washing off and removing the unreacted DNA probe and determining whether any labelling substance remains.

At the present time non-radioisotope systems are most widely used due to equipment and safety considerations, and one example thereof is the so-called digoxigenin (DIG) system disclosed in Japanese Unexamined Patent Publication No. 1-215300.

In this system, digoxigenin is used as the labelling substance attached to the DNA probe, and the labelling is detected by binding an alkali phosphatase-attached anti-digoxigenin antibody to the digoxigenin, and then detecting coloration of the substrate due to the alkali phosphatase catalytic reaction.

For labelling of the DNA probe with DIG in this DIG system, DIG-labelled uracil is mixed at a prescribed proportion with any of 4 nucleotides-adenine, guanine, thymine and cytosine, for example with thymine, constituting the DNA, and the DNA probe is synthesized with these nucleotides.

There has been shown to be an optimum value for the mixing ratio of [labelled uracil] to [the thymine] during synthesis of the probe (hereinafter referred to as the "label mixing ratio").

Mixing ratio of labelled nucleotide=[Labelled uracil]/[Thymine] [ ]: μmol/L

In other words, with an equal ratio of the 4 nucleotides constituting the detecting probe, the detection sensitivity is highest when the label mixing ratio is 35% (and thus the labelling ratio, i.e. the ratio of [labelled uracil] to [the total nucleotides] of the DNA probe, is theoretically about 6%), while sensitivity is poor with other label mixing ratios. Therefore if the labelling ratio is not kept constant for this method, the resulting lower detecting sensitivity and instability can lead to erroneous positive or negative results.

labeling ratio=[Labelled uracil]/[Total nucleotides]

However, since natural nucleic acids which are the object of detection do not have a constant ratio of the 4 nucleotides, the label mixing ratio must be adjusted each time by calculation to ensure the optimum labelling ratio, and this creates a major inconvenience. When a DNA probe is synthesized by polymerase reaction with a DNA templete, it is afraid that even adjustment of the label mixing ratio cannot equalize length of the probes produced by the enzyme reaction, and can not give the intended labelling ratio. Inability to predict the detection sensitivity when the nucleic acid has an unknown ratio of the 4 nucleotides inevitably leads to an uncertain judgment.

It is, therefore, an object of the present invention to provide a method of detecting nucleic acid which does not result in lower detecting sensitivity or instability due to differences in the labelling ratio or the nature of the nucleotide sequence of the DNA probe.

SUMMARY OF THE INVENTION

In the course of research aimed at accomplishing the above-mentioned object, a completely new discovery has been made that when gibberellin or a derivative thereof is used instead of DIG as the hapten (which is used as the substance for labelling the DNA probe according to the invention), a stable detecting sensitivity is achieved regardless of the labelling ratio, so long as the labelling ratio is at least the minimum allowed by the detecting apparatus. Note that the labelling ratio is a ratio of [the bulelled bases] to [the total bases] in a probe DNA regardless of the kind of the labeled base (adenine, guanine, cytosine and thymine (uracil)).

The present invention, therefore, provides a method of detecting nucleic acid utilizing hybridization between a nucleic acid to be detected which is present on an immobilizing support and a DNA probe which is complementary to at least a portion of the desired nucleotide sequence of the nucleic acid, comprising the steps of:

reacting a nucleic acid to be detected with a DNA probe having a hapten through a binder to obtain a hybrid between said nucleic acid and said DNA proble;

removing an unreacted DNA probe from said hybrid; and binding a labelled anti-hapten antibody with said hapten of said DNA probe in said hybrid for detecting said nucleic acid, said hapten being giblerellin or a gibberellin derivative.

The present invention further provide a method of detecting nucleic acid utilizing hybridization between nucleic acid to be detected which is present on an immobilizing support and a DNA probe which is complementary to at least a portion of the desired nucleotide sequence of the nucleic acid, comprising the steps of:

reacting a nucleic acid to be detected with a DNA probe having a hapten through a linker to obtain a hybrid between said nucleic acid and said DNA probe;

removing an unreacted DNA probe from said hybrid;

binding an anti-hapten antibody with said hapten of said DNA probe in said hybrid for detecting said nucleic acid, said hapten being gibberellin or a gibberallin derivative; and then binding said bound anti-hapten antibody with a labelled antibody capable specifically binding to said anti-hapten antibody.

The present invention makes it possible to achieve a stable detecting sensitivity regardless of the labelling ratio or label mixing ratio, and thus regardless of the nature of the base sequence of the DNA probe, so long as the labelling ratio is at least the minimum allowed by the detecting apparatus. It therefore becomes possible to judge accurately whether the nucleic acid of interest is present or not.

DETAILED DESCRIPTION OF THE INVENTION

Figure 1:
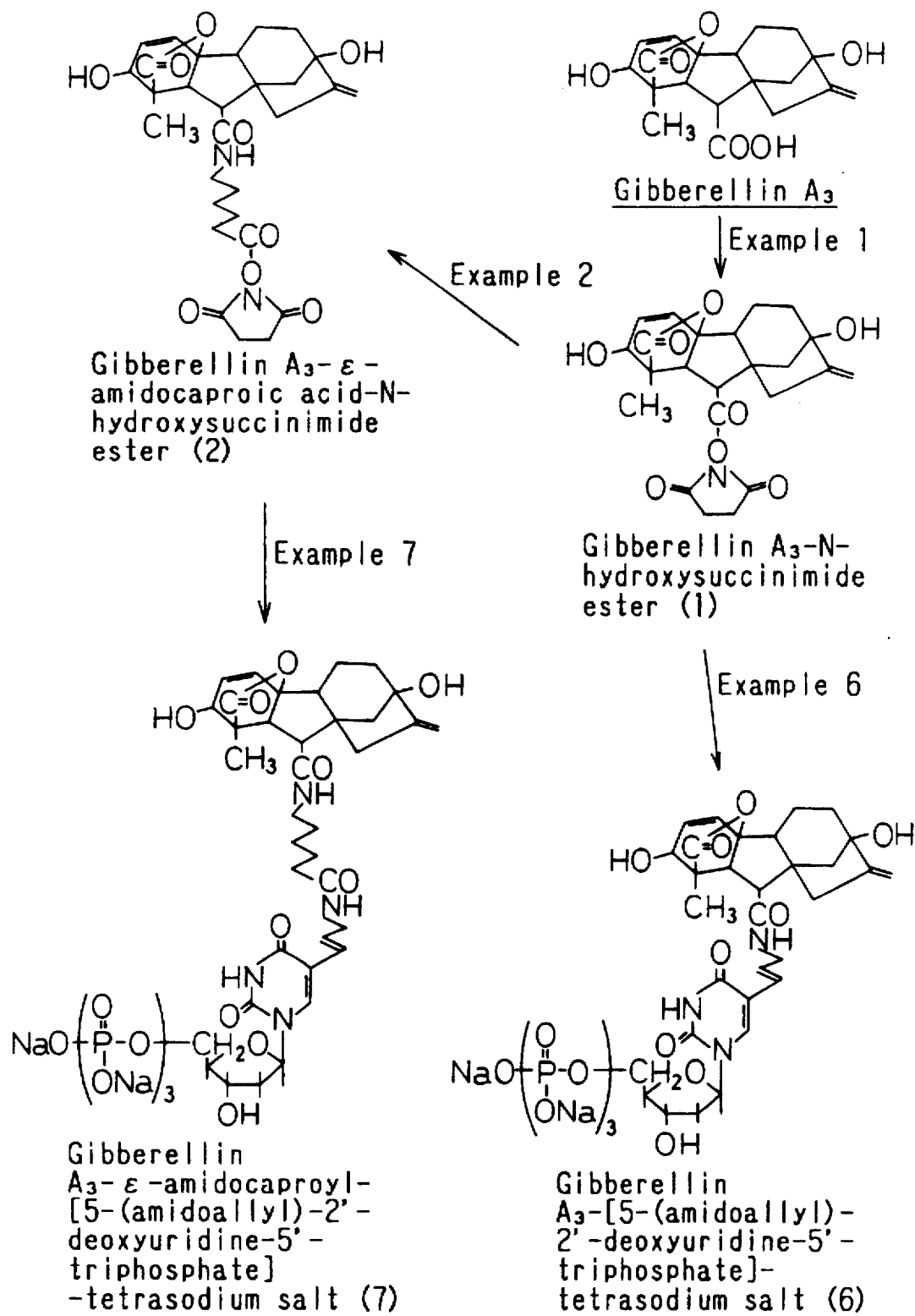
FIG. 1 is a system diagram for substances in the examples of the invention.

According to the present invention, gibberellin or a derivative thereof is used as the labelling hapten, and it may be any naturally occurring gibberellin (GA) such as $GA_1$, $GA_2$, $GA_3$, $GA_4$, etc. or any non-natural GA derivative which has undergone chemical modification or removal of a functional group so long as the gibberellin skeleton is not altered, and these may include substances which do not exhibit the physiological activity of gibberellin.

The labelling hapten is linked to the DNA probe via a linker. The nucleotide of the DNA probe to which the linker is attached may be adenine, guanine, cytosine or thymine, and uracil may be used instead of thymine. Preferred linking sites on the DNA probe for linking, for example on the bases of the nucleotides making up the DNA probe, include position 8 of the purine base and position 5 of the pyrimidine base.

Preferred linker attachment sites on the gibberellin or its derivative include the carboxyl group at position 6, the ketone group at position 16 and the hydroxyl group at position 3 of the compound. The linker is a structure having both groups able to bind to the susceptible group of the DNA probe and a group able to bind to the binding group of the gibberellin or its derivative, and examples of susceptible groups on the linker include amino groups which form amide bonds with the carboxyl group of the gibberellin or its derivative or amino groups which form imino bonds though reaction with a ketone group introduced into the gibberellin or its derivative.

The linker must be at least long enough to avoid "steric hindrance" during the hapten-antibody reaction, and it is preferably at least 4 atoms long including the atoms in the above-mentioned susceptible groups. A preferred linker is allylamine which itself may serve as the linker, and can bind to position 8 of the purine base or position 5 of the pyrimidine base, which are the linking sites for the above-mentioned linker.

Also, in order to further lengthen the size of the linker, there may also be used a compound comprising an aliphatic chain with a carboxyl group at one end which is attachable to the allylamine group already attached to the base as the linker, and an amino group at the other end. The aliphatic group in this case has 2 to 10 carbon atoms, and preferably 4 to 7, more preferably 5. Preferred examples thereof include 6-aminocaproic acid, 4-aminopropionic acid and 4-aminobutyric acid.

The anti-hapten antibody to be used according to the invention may be an antibody produced using the hapten, gibberellin or its derivative, as the antigen, and it may be either a polyclonal or monoclonal antibody. Methods for preparing polyclonal or monoclonal antibodies using haptens as antigenic portions are well-known, and any known method may be employed. The animal used to produce the polyclonal antibodies may be, for example, a rabbit, guinea pig, mouse, goat, or the like.

According to a first embodiment of the present invention, the above-mentioned antibody is linked to the label which is used to detect it. The label may be an enzyme, for example an enzyme which promotes a coloration reaction, luminescent reaction or fluorescent reaction. Examples of enzymes which promote coloration reactions are alkaline phosphatase, β-galactosidase, peroxidase, and so on, enzymes which promote luminescent reactions are luciferase, peroxidase, and so on, and enzymes for fluorescent reactions include alkaline phosphatase, peroxidase, esterase, and so on. A colorimetric substrate, luminescent substrate or fluorescent substrate is used for detection of these enzymes, depending on the type of enzyme. The enzyme, substrate, reaction, and so on used for the detection may be those employed in conventional methods.

According to a second embodiment of the present invention, the anti-hapten antibody may be detected using a labelled antibody (secondary antibody) against the anti-hapten antibody, without direct labelling of the anti-hapten antibody (primary antibody). If a certain type of animal antibody, for example, is used as the anti-hapten antibody (primary antibody), another antibody (secondary antibody) which binds specifically to that type of antibody may be used. For example, if the primary antibody is a mouse antibody as the anti-hapten antibody, then the secondary antibody may be a rabbit antibody which is specific for mouse antibodies.

According to this embodiment, the label which binds to the secondary antibody for detection of the secondary antibody and the method for the detection are the same as for detection of the anti-hapten antibody in the first embodiment.

The intact antibody may be used directly as the above-mentioned primary and/or secondary antibody, or a fragment of the antibody, such as $F(ab')_2$, Fab', and so on, which retains bindability, may also be used. The fragmentation may be accomplished by a conventional method.

According to the method of the invention, any known immobilizing support may be used as the solid support for immobilization of the nucleic acid to be detected. The support is generally in a convenient form to be easily immersed in the hapten-antibody reaction solution, and of a substance with low non-specific binding to antibodies and proteins, which is a source of background noise; specific examples thereof include nitrocellulose filters, nylon filters, plastic, plexiglass, nitrocellulose- and nylon-coated plastic and plexiglass, etc.

To carry out the present invention, nucleic acid in a test sample is first immobilized on the surface of a solid support. The nucleic acid may be either DNA or RNA. The immobilization may be accomplished in any conventional manner. It may be accomplished, for example, by UV irradiation, heating at 80° C. for 2 hours, or vacuum blotting. In the case of vacuum blotting, a buffer solution such as 0.5N NaOH, 2×SSC, TE or the like may be used as the medium for the immobilization reaction conducted, for example, at room temperature to 37° C. for 5 minutes.

The support is then immersed in the hybridization solution for prehybridization. The composition of the hybridization solution may be, for example, a 1% aqueous casein solution (buffer: 0.1M Tris-HCl, 150 mM NaCl, pH=7.5), used for treatment at 42° to 70° C. for 1 to 16 hours.

Hybridization is then performed by treating the solid support with a hybridization solution containing the DNA probe. The hybridization solution used here may have a composition of, for example, 10×SSC, 5% casein, 5% N-lauroylsarocosine and 5% SDS. The hybridization conditions will differ depending on the length of the DNA probe, etc., but are generally at 42° C. to 70° C. for 1 to 18 hours.

Next, since the hapten is attached to the DNA probe, according to the first embodiment of the invention the hapten is bound to the labelled anti-hapten antibody. The reaction may be conducted under normal conditions, for example in a Tris buffer solution (pH 7.5) or phosphate buffer solution, at 20° to 37° C., for 15 to 60 minutes. Then, after washing the solid support with a washing solution such as a Tris buffer solution (pH 7.5) to remove the unbound labelled antibody, in cases where the labelling of the antihapten antibody is an enzyme it is reacted with an enzyme-coloring substrate to produce a color.

The reaction medium used here is, for example, a Tris buffer solution (pH 7.5). The coloring will differ depending on the labelling enzyme and the substrate, but is generally performed by allowing the solution to stand for an appropriate time at 20° to 37° C.

According to an another embodiment of the invention, the detection is accomplished using a labelled antibody against the anti-hapten antibody without labelling the anti-hapten antibody. The anti-hapten antibody (primary antibody) may be reacted with the labelled antibody (secondary antibody), for example, in a medium such as a Tris buffer solution (pH 7.5), at 20° to 37° C. for 15 to 60 minutes.

Next, after washing the solid support with a washing solution such as a Tris buffer solution (pH 7.5) to remove the unbound labelled antibody (secondary antibody), in cases where the labelling of the secondary antibody is an enzyme it is reacted with a coloring substrate to produce a color. The coloring in this case may be accomplished in the same manner as the first embodiment.

EXAMPLES

The present invention will now be explained in more detail by way of the following examples. The reaction systems for Examples 1 to 8 are shown in FIGS. 1 and 2.

Example 1

Figure 2:
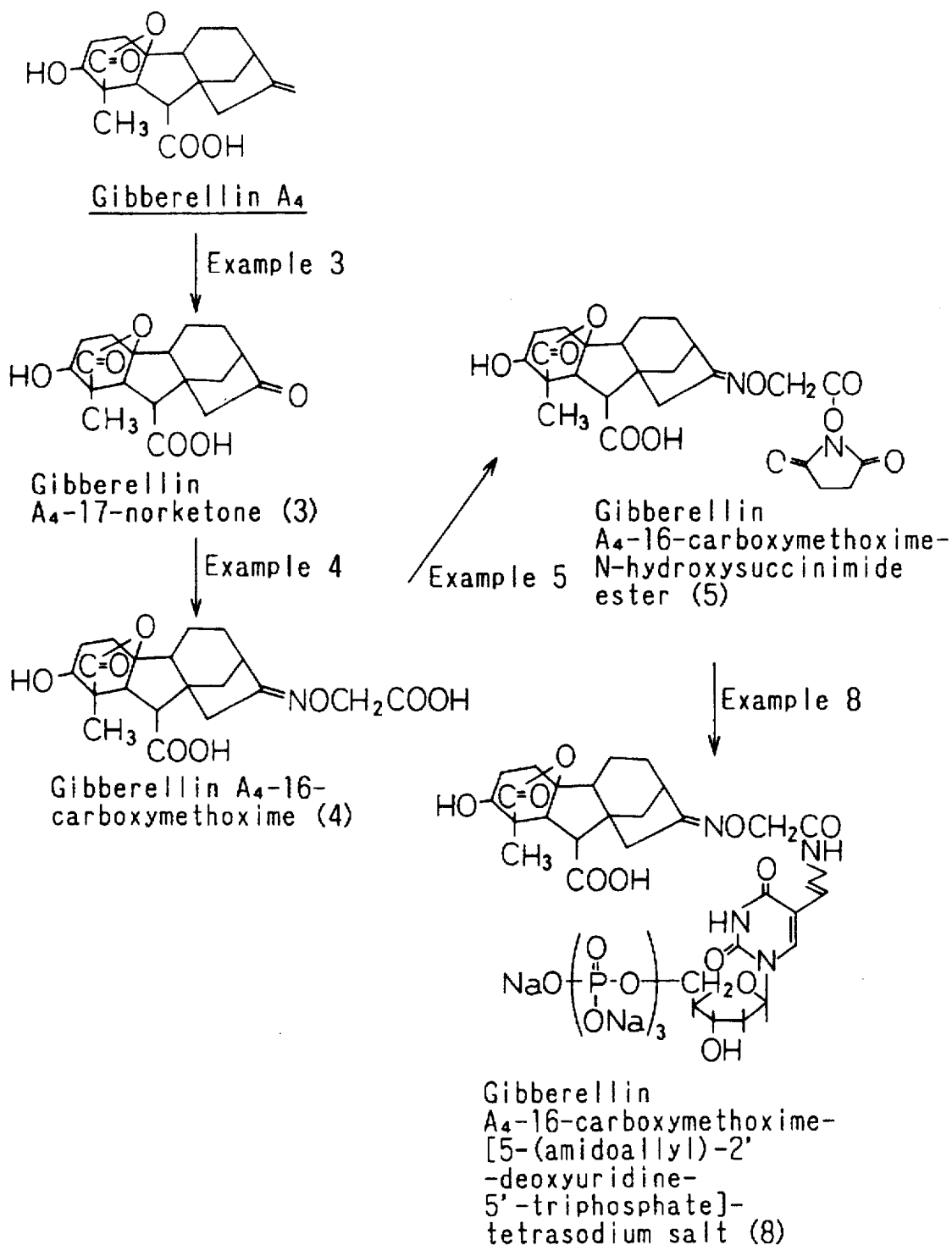
FIG. 2 is a system diagram for substances in the examples of the invention.

Synthesis of gibberellin $A_3$-N-hydroxysuccinimide ester (gibberellin $A_3$ with activated linker-binding site) (see, FIG. 1)

In a 50 ml rounded flask, 2 g (5.8 mmol) of gibberellin $A_3$ and 668 mg (5.8 mmol) of N-hydroxysuccinimide were dissolved in 20 ml of dioxane, and then 1.3 ml (5.8 mmol) of dicyclohexylcarbodiimide was added and the mixture was stirred at room temperature for 2–3 hours. The precipitating dicyclohexylurea was removed by filtration, and the dioxane was evaporated off under an oil pump vacuum. The oily residue was dissolved in 10 ml of ethyl acetate and then poured into 50 ml of petroleum ether, upon which crystals precipitated. The crystals were dried under a vacuum. This produced 2.07 g (80% yield).

Example 2

Synthesis of gibberellin $A_3$-ε-amidocaproic acid-N-hydroxysuccinimide ester (gibberellin $A_3$ attached to end-activated linker) (see FIG. 1)

In a 30 ml rounded flask, 360 mg (0.80 mmol) of gibberellin $A_3$-N-hydroxysuccinimide ester was dissolved in 3.6 ml of dimethylsulfoxide, and after successively adding 213 mg of 6-aminocaproic acid dissolved in 1.8 ml water and 0.22 ml of triethylamine, the mixture was stirred at room temperature overnight. The solvent was evaporated off under a vacuum and the oily residue was dissolved in 2 ml of dimethylsulfoxide, after which a reverse phase column was used for elution with water and acetonitrile to separate the product. This was dried under a vacuum and used for the next reaction.

The resultant gibberellin $A_3$-ε-amidocaproic acid was dissolved in 3 ml of anhydrous dimethylformamide, and then 115 mg (1.0 mmol) of N-hydroxysuccinimide and 0.22 ml (1.0 mmol) of dicyclohexylcarbodiimide were successively added and the mixture was reacted at room temperature overnight. After removing the precipitated dicyclohexylurea by filtration and evaporating off the solvent under a vacuum, the resultant oily substance was suspended in ethyl acetate and poured into petroleum ether for crystallization. The crystals were collected and dried under a vacuum. This produced 174 mg (38% yield).

The following Examples 3 to 5 relate to activation of the linker-binding site of gibberellin $A_4$ and attachment of the linker.

Example 3

Synthesis of gibberellin $A_4$-17-norketone (see, FIG. 2)

In a 30 ml rounded flask, 100.6 mg (0.30 mmol) of gibberellin $A_4$ was dissolved in 10 ml of tetrahydrofuran/$H_2O$ (1:1), and then 15.2 mg (0.06 mmol) of osmium oxide was added while cooling on ice. After stirring for 10 minutes, 217.2 mg (1.02 mmol) of sodium periodate was added, and after inclusion of $N_2$ gas the mixture was stirred overnight at room temperature. The precipitate was filtered from the reaction solution, the filtrate was concentrated under reduced pressure at 40° C. to distill off the tetrahydrofuran, and after the resulting aqueous solution was adjusted to pH 1.5 by addition of 2 drops of 6N sulfuric acid, followed by extracting 3 times with a total of 25 ml of ethyl acetate. The resultant ethyl acetate extract was dehydrated by addition of anhydrous sodium sulfate and cooling overnight, after which the anhydrous sodium sulfate was filtered off and the solution was concentrated.

This was purified by silica gel (3 g) adsorption chromatography. The eluent used was a chloroform-ethyl acetate elution system, and ethyl acetate was increased in increments of 5% from 100% chloroform. Ten milliliters of eluate was separated off per step. Gibberellin $A_4$-17-norketone eluted in the 20%–55% ethyl acetate fraction. This was recrystallized with an acetone/hexane system to obtain 75 mg of gibberellin $A_4$-17-norketone.

This synthesis was performed according to the method in M. Nakajima et al., Plant Cell Physiol. 32(4), 505–510 (1991).

Example 4

Synthesis of gibberellin $A_4$-16-carboxymethoxim (see, FIG. 2)

In a 10 ml rounded flask, 25.5 mg (0.23 mmol) of carboxymethoxylamine hydrochloride was dissolved in 0.68 ml of pyridine. To this 30 mg (0.09 mmol) of gibberellin $A_4$-17-norketone was added and the mixture was heated to 50° C. and allowed to stand for 3 hours.

The reaction solution was passed through 20 ml of ice-cooled 0.5% HCl, the pH was adjusted to 3.5 with HCl, followed by extracting 3 times with a total of 150 ml of ethyl acetate. The resultant ethyl acetate extract was washed twice with a total of 200 ml, anhydrous sodium sulfate containing 0.5% HCl was added, the mixture was cooled overnight for dehydrating, and then the anhydrous sodium sulfate was filtered off, the filtrate was concentrated, and the residue was recrystallized with an acetone/hexane system to obtain 22.2 mg of gibberellin $A_4$-16-carboxymethoxim.

The synthesis was performed according to the method in M. Nakajima et al., Plant Cell Physiol. 32(4), 505–510 (1991).

Example 5

Synthesis of gibberellin $A_4$-16-carboxymethoxim-N-hydroxysuccinimide ester A 5 mg (0.012 mmol) portion of gibberellin $A_4$-16-carboxymethoxim was dissolved in 83 µl of dimethylsulfoxide, and then 14 µl (0.012 mmol) of N-hydroxysuccinimide dissolved in dimethylsulfoxide to a concentration of 100 mg/ml was added, 2.7 µl (0.012 mmol) of dicyclohexylcarbodiimide was added and the mixture was reacted overnight at room temperature. The precipitated dicyclohexylurea was removed by filtration, and the resulting solution was used in the next reaction.

Example 6

Synthesis of gibberellin $A_3$-[5-(amidoallyl)-2'-deoxyuridine-5'-triphosphate]-tetrasodium salt (hapten-attached base (labelled base)) (see, FIG. 1)

A 4 mg (9.0 µmol) portion of gibberellin $A_3$-N-hydroxysuccinimide ester was dissolved in 100 µl of dimethylsulfoxide, and the solution was added to 0.9 ml of a 0.1M sodium borate solution (pH 8.5) in which 2.05 µmol of 5-allylamino-2'-deoxyuridine-5'-triphosphatetetrasodium salt had been dissolved and the mixture was allowed to stand at room temperature overnight.

The desired substance was separated from the reaction mixture by HPLC chromatography, using a linear concentration gradient of 0M to 0.7M sodium chloride solution, with TSK gel DEAE-2SW in a filled column for high-speed ion exchange chromatography (Toso). The peak of the desired substance has a slower retention time than 5-allylamino-2'-deoxyuridine-5'-triphosphate and is thus clearly distinguishable. The fraction containing the peak of the pure substance was collected, desalted with Sephadex G-10 and lyophilized to obtain the desired substance.

In this product, the carbaminopropenyl group between gibberellin $A_3$ and uridyl serves as the linker.

Example 7

Synthesis of gibberellin $A_3$-ε-amidocaproyl-[5-(amidoallyl)-2'-deoxyuridine-5'-triphosphate]-tetrasodium salt (hapten-attached nucleotide (labelled nucleotide)) (see, FIG. 1)

A 10 mg (10.5 µmol) portion of gibberellin $A_3$-ε-amidocaproic acid-N-hydroxysuccinimide ester was dissolved in 155 µl of dimethylsulfoxide, and the solution was added to 1.4 ml of a 0.1M sodium borate solution (pH 8.5) in which 4.2 µmol of 5-allylamino-2'-deoxyuridine-5'-triphosphate-tetrasodium salt had been dissolved and the mixture was allowed to stand at room temperature overnight.

In the same manner as in Example 6, the separation from the reaction mixture was performed by HPLC chromatography, using a linear concentration gradient of 0M to 0.7M sodium chloride solution, with TSK gel DEAE-2SW in a filled column for high-speed ion exchange chromatography (Toso). The peak of the desired substance has a slower retention time than 5-allylamino-2'-deoxyuridine-5'-triphosphate and is thus clearly distinguishable. The fraction containing the peak of the pure substance was collected, desalted with Sephadex G-10 and lyophilized to obtain the desired substance.

Example 8

Synthesis of gibberellin $A_4$-16-carboxymethoxim-[5-(amidoallyl)-2'-deoxyuridine-5'-triphosphate]-tetrasodium salt (hapten-attached nucleotide (labelled nucleotide)) (see, FIG. 8)

A 34 µl (4 µmol) portion of the gibberellin $A_4$-16-carboxymethoxim-N-hydroxysuccinimide ester reaction solution of Example 5 was added to 0.42 ml of a 0.1M sodium borate solution (pH 8.5) in which 1 µmol of 5-allylamino- 2'-deoxyuridine-5'-triphosphate-tetrasodium salt had been dissolved and the mixture was allowed to stand at room temperature overnight.

In the same manner as in Example 6, the separation from the reaction mixture was performed by HPLC chromatography, using a linear concentration gradient of 0M to 0.7M sodium chloride solution, with TSK gel DEAE-2SW in a high-speed ion exchange chromatography filled column (Toso). The peak of the desired substance has a slower retention time than 5-allylamino-2'-deoxyuridine-5'-triphosphate and is thus clearly distinguishable. The fraction containing the peak of the pure substance was collected, desalted with Sephadex G-10 and lyophilized to obtain the desired substance.

Example 9

Synthesis of gibberellin $A_3$-labelled bovine serum albumin

A 30 mg portion of gibberellin $A_3$ was dissolved in 150 µl of dimethylformamide, and the solution was mixed with 30 mg of N-hydroxysuccinimide dissolved in 75 µl of dimethylformamide and 38 mg of dicyclohexylcarbodiimide dissolved in 75 µl of dimethylformamide, and stirred for 3.5 hours at room temperature. The supernatant from centrifugation was added to a bovine serum albumin solution (30 mg/3 ml 100 mM sodium phosphate buffer solution, pH=7.5), and the mixture was allowed to stand on ice for 2 hours. After further centrifugation the supernatant was dialyzed against a 50 mM sodium phosphate buffer solution (pH=7.0). This was lyophilized to obtain the desired substance.

Example 10

Preparation of gibberellin $A_3$ antiserum

A 25 mg portion of gibberellin $A_3$-labelled bovine serum albumin was dissolved in 5 ml of PBS (phosphate-buffered saline), a same amount of an emulsifier was added, and the resultant emulsion was used to immunize 3 rabbits once a week. After the 7th immunization, whole blood was taken and gibberellin $A_3$ antiserum was obtained.

Example 11

Purification of anti-gibberellin $A_3$ antibody from antiserum

After diluting 45 ml of the antiserum with a same amount of 0.15M NaCl, 34 g (50% saturated amount) of ammonium sulfate was added and the resulting solution was allowed to stand at 4° C. for one hour. The precipitate collected from centrifugation was dissolved in 45 ml of 0.0175M sodium phosphate buffer solution (pH=6.3), and this was dialyzed against 1L of 0.0175M sodium phosphate buffer solution (pH=6.3). The solution was passed through a column (2.5× 10 cm) of DEAE Sephacell (Pharmacia) which had been equilibrized with the above-mentioned buffer solution, and the final fraction which passed through was concentrated by ultrafiltration.

The concentrate was flowed at a rate of 7 ml/h through an affinity gel column (1×10 cm) filled with EAH-Sepharose 4B (Pharmacia) to which gibberellin $A_3$ was bound, and then the column was washed with 30 ml of a phosphate buffer solution (0.1M, pH=7.5). Next, 20 ml of 1M propionic acid (pH=3.5) containing 0.1% polyethylene glycol lauryl ether was flowed through the column, and 0.5 ml portions of the eluate was fractionated into 40 tubes each already containing 1 ml of 1M N-(2-hydroxyethyl)piperazine-N'-2-ethanesulfonic acid (pH=7.5), and the eluted fractions were collected to obtain the anti-gibberellin $A_3$ antibody.

Example 12

Preparation of alkaline phosphatase-labelled anti-gibberellin $A_3$ antibody A 3 mg (0.4 ml) portion of the anti-gibberellin $A_3$ antibody was dialyzed with a 0.1M acetic acid-sodium hydroxide buffer solution (pH 4.5), 1 mg of pepsin was added, and the mixture was allowed to stand at 37° C. for 16 hours. The precipitate was removed by centrifugation, and after gel filtration (Ultrogel AcA44, 1×45 cm, 0.1 M phosphoric acid-sodium hydroxide buffer solution, pH=6), the protein fractions having approximately the corresponding molecular weight were collected and concentrated to 0.4 ml by ultrafiltration.

70 µl of 0.1M mercaptoethylamine (0.1M phosphoric acid-sodium hydroxide buffer solution, pH=6, 5 mM EDTA) was added to the obtained concentrate, and the mixture was allowed to stand at 37° C. for 90 minutes. After gel filtration (Ultrogel AcA44, 1×45 cm, 0.1M phosphoric acid-sodium hydroxide buffer solution, pH=6, 5 mM EDTA), the protein fractions having approximately the corresponding molecular weight were collected, concentrated to 0.4 ml by ultrafiltration, and used as the Fab' solution.

200 µl of 1M phosphoric acid-sodium hydroxide buffer solution (pH=7) and 30 µl of N-sulfosuccinimidyl-4-(N-maleimidomethyl)-cyclohexane-1-carboxylate (sulfo-SMCC, 5 mg/250 µl DMSO) were added to 1 mg of alkaline phosphatase (100 µl, 3M sodium chloride, 1 mM manganese chloride, 0.1 mM zinc chloride, 30 mM triethanolamine, pH=7.6, Berlinger Co.), followed by standing at 30° C. for 60 minutes and centrifugation, the mixture was desalted by gel filtration (Sephadex G-25, 1×15 cm, 0.1M phosphoric acid-sodium hydroxide, pH=6), and the protein fractions were collected and concentrated to 0.4 ml by ultrafiltration.

The obtained concentrate was mixed with 0.2 ml of the previously prepared Fab' solution and allowed to stand at 30° C. for 60 minutes, and after addition of 10 µl of 50 mM N-ethylmaleimide and gel filtration (Ultrogel AcA44, 1×45 cm, 0.1M phosphoric acid-sodium hydroxide buffer solution, pH=6.5), the protein fractions having approximately the corresponding molecular weight were collected and used as the alkaline phosphatase-labelled anti-gibberellin $A_3$ solution.

The preparation method was carried out according to the enzyme immunoassay method (Igaku Shoin, ed. Ishikawa, Eiji et al.).

Example 13 Preparation of gibberellin $A_4$-labelled detection probe (label mixing ratio: 35%)

In this example, a DNA probe was prepared using a DNA sample with a specific base sequence (pBR322) as the template.

After mixing 8 µl of pBR322 (1 µg/µl, Takara Shuzo), 8 µl of HindIII (Takara Shuzo), 6.4 µl of buffer M×10 (Takara Shuzo) and 57.6 µl of water and allowing the mixture to stand at 37° C. for 60 minutes, a washing procedure involving addition of 80 µl of phenol/chloroform and collection of the supernatant from centrifugation was repeated twice. After adding 8 µl of 3M sodium acetate (pH=9) and 240 µl of cold ethanol, allowing the mixture to stand at −70° C. for 60 minutes and, the supernatant was removed by centrifugation, 100 µl of cold 70% ethanol was added to the precipitate and the precipitate obtained upon further centrifugation was vacuum dried.

After adding 100 µl of water, heating at 95° C. for 10 minutes and cooling on ice, 6 µl of hexanucleotide (Berlinger), 9 µl of a $GA_4$-labelled mixture [27 µl of 0.26 mM gibberellin $A_4$-16-carboxymethoxim-[5-(amidoallyl)-2'-deoxyuridine-5'-triphosphate]-tetrasodium salt, 2 µl of 10 mM deoxyguanosine-5'-triphosphate, 2 µl of 10 mM deoxyadenosine-5'-triphosphate, 2 µl of 10 mM deoxycytidine-5'-triphosphate, 2 µl of 6.7 mM deoxythymidine-5'-triphosphate] and 3 µl of Klenow enzyme (Berlinger) were added and the mixture was allowed to stand at 37° C. for 10 hours. Then, after adding 6 µl of 0.2M EDTA (pH=8), 6 µl of 3M lithium chloride and 360 µl of cold ethanol and allowing the mixture to stand at −70° C. for 60 minutes, the resultant supernatant was removed by centrifugation, 100 µl of cold 70% ethanol was added to the precipitate, and the precipitate obtained by further centrifugation was vacuum dried to obtain the desired substance.

Example 14

Comparison of Effects of Labelling Ratios on Detection Sensitivity

The DNA probe of the invention and the DIG DNA probe (comparative example) were prepared to various label mixing ratios, and a detection sensitivity was tested on DNA samples.

After heat denaturation of pBR322 at 95° C. for 10 minutes, solutions of 0.05 pg/2 µl, 0.1 pg/2 µl, 0.2 pg/2 µl, 0.5 pg/2 µl, 1 pg/2 µl and 10 pg/2 µl were prepared using a DNA diluting buffer (50 µg/µl salmon sperm DNA, 10 mM Tris-HCl, 1 mM EDTA, pH=8), and each was spotted on 10 nylon films. The samples were UV-irradiated for 5 minutes to immobilize the DNA on the film, immersed in a hybridization solution (0.5% blocking reagent (Berlinger), 0.1% N-laurylsarcosine, 0.02% SDS, 0.75M sodium chloride, 75 mM citric acid, pH=7) and then shaken at 68° C. for 4 hours.

Label mixing ratios of 20%, 35%, 50%, 75% and 100% were prepared according to the method in Example 13, while the gibberellin $A_4$-16-carboxymethoxim-[5-(amidoallyl)-2'-deoxyuridine-5'-triphosphate]-tetrasodium salt in the $GA_4$-labelled mixture of Example 13 was replaced with digoxigenin-11-uridine-5'-triphosphate (Berlinger), preparing label mixing ratios of 20%, 35%, 50%, 75% and 100%.

The 10 solutions were then made into 26 ng/ml hybridization solutions, and the 10 nylon films prepared earlier were immersed therein and shaken at 68° C. for 6 hours. After washing twice at room temperature for 5 minutes using 0.3M sodium chloride and 30 mM citric acid (pH=7) and then washing twice at 68° C. for 15 minutes using 15 mM sodium chloride and 1.5 mM citric acid (pH=7), the nylon films on which the gibberellin $A_4$-labelled DNA had been immobilized were immersed in alkaline phosphatase-labelled anti-gibberellin $A_4$ antibody (0.2 µg/ml, 0.1M Tris-HCl, 0.15M NaCl, pH=7.5) prepared in the same method as in Example 12, while the nylon films on which the DIG-labelled DNA had been immobilized were immersed in alkaline phosphatase-labelled anti-DIG antibody (Berlinger, 0.2 ug/ml, 0.1M Tris-HCl, 0.15M NaCl, pH=7.5), and the immersions were shaken for 30 minutes at room temperature.

After immersion in a Tris buffer (0.1M Tris-HCl, 0.15M NaCl, pH=7.5) and shaking and washing twice for 15 minutes, the nylon films were immersed in a coloring reagent [45 μl 4-nitroblue tetrazolium chloride (Berlinger), 35 μl 5-bromo-4-chloro-3-indolyl phosphate (Berlinger), 0.1M Tris-HCl, 0.1M NaCl, 0.05M $MgCl_2$, pH 9.5, 10 ml] and placed in a dark area for 20 hours. The nylon films were washed with water and dried. The appearance of colored spots was visually examined.

Table 1 shows the maximum detection sensitivities based on the results.

TABLE 1

| | Maximum detection sensitivity for each labelling ratio | | | | |
|---|---|---|---|---|---|
| | Mixing ratio | | | | |
| Labelling | 20% | 35% | 50% | 75% | 100% |
| Gibberellin $A_4$-labelled | 0.2 pg | 0.1 pg | 0.1 pg | 0.1 pg | 0.1 pg |
| DIG-labelled | 0.2 pg | 0.1 pg | 0.2 pg | 0.5 pg | 1.0 pg |

It is clear from Table 1 that the maximum detection sensitivity with the DIG-labelled DNA varied depending on the label mixing ratio, but with the gibberellin-labelled DNA it was almost constant.

We claim:

1. A method of detecting a nucleic acid, comprising:
   hybridizing a DNA probe to a nucleic acid to produce a probe-nucleic acid hybrid, wherein
   the DNA probe is at least partially complementary to the nucleic acid, and is labeled with a gibberellin, and
   the nucleic acid is immobilized on a solid support;
   binding a labeled anti-gibberellin antibody to the gibberellin in the probe-nucleic acid hybrid; and
   detecting the labeled antibody and thereby the nucleic acid.

2. A method of detecting a nucleic acid, comprising:
   hybridizing a DNA probe to a nucleic acid to produce a probe-nucleic acid hybrid, wherein
   the DNA probe is at least partially complementary to the nucleic acid, and is labeled with a gibberellin; and
   the nucleic acid is immobilized on a solid support;
   binding an anti-gibberellin antibody to the gibberellin in the probe-nucleic acid hybrid; and
   binding a labeled antibody to the anti-gibberellin antibody, wherein the labeled antibody is specific for the anti-hapten antibody; and
   detecting the labeled antibody and thereby the nucleic acid.

3. The method of claim 1 wherein the gibberellin is a naturally-occurring gibberellin or a non-natural gibberellin obtained by removing or modifying a functional group of a naturally-occurring gibberellin without modifying the gibberellin skeleton.

4. The method of claim 3, wherein the gibberellin has a carboxymethoxime group at the 16 position.

5. The method of claim 1, wherein the gibberellin is a naturally-occurring gibberellin selected from the group consisting of $GA_1$, $GA_2$, $GA_3$ and $GA_4$.

6. The method of claim 1, wherein the gibberellin is physiologically active.

7. The method of claim 1, wherein the gibberellin is chemically bonded to the DNA probe by a linker.

8. The method of claim 7, wherein the linker is chemically bonded to the DNA probe at the 8-position of a purine base or the 5-position of a pyrimidine base.

9. The method of claim 7, wherein the linker is chemically bonded to the gibberellin at the carboxyl group at the 6-position, the carbon atom at the 16 position or a hydroxyl group at the 3-position.

10. The method of claim 7, wherein the linker comprises a carboxymethoxime group that is bonded to the carbon atom at the 16 position of the gibberellin.

11. The method of claim 7, wherein the linker has a length of at least 4 carbon atoms.

12. The method of claim 2, wherein the gibberellin is a naturally-occurring gibberellin or a non-natural gibberellin obtained by removing or modifying a functional group of a naturally-occurring gibberellin without modifying the gibberellin skeleton.

13. The method of claim 2, wherein the gibberellin has a carboxymethoxime group at the 16 position.

14. The method of claim 2, wherein the gibberellin is a naturally-occurring gibberellin selected from the group consisting of $GA_1$, $GA_2$, $GA_3$ and $GA_4$.

15. The method of claim 2, wherein the gibberellin is physiologically active.

16. The method of claim 2, wherein the gibberellin is chemically bonded to the DNA probe by a linker.

17. The method of claim 16, wherein the linker is chemically bonded to the DNA probe at the 8-position of a purine base or the 5-position of a pyrimidine base.

18. The method of claim 16, wherein the linker is chemically bonded to the gibberellin at the carboxyl group at the 6-position, the ketone group at the 16 position or the hydroxyl group at the 3-position.

19. The method of claim 16, wherein the linker comprises a carboxymethoxime group that is bonded to the carbon atom at the 16 position of the gibberellin.

20. The method of claim 16, wherein the linker has a length of at least 4 carbon atoms.

* * * * *